(12) United States Patent
Veiner

(10) Patent No.: US 7,264,111 B2
(45) Date of Patent: Sep. 4, 2007

(54) MAGNETIC SPECIMEN-TRANSPORT SYSTEM FOR AUTOMATED CLINICAL INSTRUMENT

(75) Inventor: Craig R. Veiner, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/377,127

(22) Filed: Mar. 16, 2006

(65) Prior Publication Data

US 2006/0177346 A1   Aug. 10, 2006

Related U.S. Application Data

(63) Continuation of application No. 10/794,686, filed on Mar. 5, 2004, now Pat. No. 7,028,831.

(51) Int. Cl.
*G01N 35/02* (2006.01)
(52) U.S. Cl. ............. 198/619; 198/465.1; 422/65
(58) Field of Classification Search ......... 198/619, 198/465.1; 422/63, 65
See application file for complete search history.

(56) References Cited

U.S. PATENT DOCUMENTS

| | | |
|---|---|---|
| 3,897,216 A | 7/1975 | Jones |
| 4,040,533 A | 8/1977 | De Boer et al. |
| 4,454,939 A | 6/1984 | Kampf et al. |
| 5,008,082 A | 4/1991 | Shaw |
| 5,687,849 A | 11/1997 | Borenstein et al. |
| 5,720,377 A | 2/1998 | Lapeus et al. |
| 5,871,084 A * | 2/1999 | Kasik .................. 198/803.6 |
| 5,906,262 A * | 5/1999 | Miki .................. 198/341.02 |
| 6,206,176 B1 * | 3/2001 | Blonigan et al. ......... 198/619 |
| 6,337,050 B1 | 1/2002 | Takahashi et al. |
| 6,571,934 B1 | 6/2003 | Thompson et al. |

FOREIGN PATENT DOCUMENTS

JP      61081323 A      4/1986

* cited by examiner

*Primary Examiner*—Mark A. Deuble
(74) *Attorney, Agent, or Firm*—Warren W. Kurz; Mitchell E. Alter

(57) ABSTRACT

A magnetic specimen-transport system for transporting racks of specimen-containers to or within an automated clinical instrument for analysis and/or processing. The magnetic specimen-transport system that is adapted to transport magnetically-attractable racks of specimen-containers in mutually perpendicular (X/Y) directions across a rack-supporting surface, whereby the racks can be transported among various non-linearly aligned positions on such surface.

14 Claims, 11 Drawing Sheets ment Clinical Workcell", and
MAGNETIC SPECIMEN-TRANSPORT SYSTEM FOR AUTOMATED CLINICAL INSTRUMENT

CROSS-REFERENCE TO RELATED APPLICATIONS

Reference is made to the following commonly assigned patent applications, the subject matter of which is incorporated herein by reference:

U.S. application Ser. No. 10/794,686 filed Mar. 5, 2004 now U.S. Pat. No. 7,028,831 entitled "Magnetic Specimen-Transport System for Automated Clinical Instrument, of which the present application is a continuing application;

U.S. application Ser. No. 10/794,702 filed Mar. 5, 2004 entitled "Specimen-Transport Module for a Multi-Instrument Clinical Workcell", and U.S. application Ser. No. 10/794,685 filed Mar. 5, 2004 entitled "Specimen-Container Rack for Automated Clinical Instrument."

BACKGROUND OF THE INVENTION

1. Field of the Invention

The present invention relates to improvements in apparatus for transporting racks of specimen-containers to or within an automated clinical instrument for analysis and/or processing. More particularly, this invention relates to a magnetic specimen-transport system that is adapted to transport magnetically-attractable racks of specimen-containers in mutually perpendicular (X/Y) directions across a rack-supporting surface, whereby the racks can be transported among various non-linearly aligned positions on such surface.

2. The Prior Art

It is known in the art to perform diagnostic tests on various liquid biological specimens, e.g., whole blood, serum, urine, spinal fluids, etc., using different automated clinical instruments. In the analysis of whole blood specimens, for example, such automated instruments often include hematology and fluorescence flow cytometry instruments that operate to count and/or differentiate different types of blood cells on the basis of their respective physical, optical and/or electrical properties. The specimens to be analyzed by such instruments are commonly collected in various types of test tubes or containers. Each container is normally sealed at its top by a puncturable rubber cap through which a movably-mounted aspiration probe of each instrument can enter and withdraw a desired aliquot of specimen for processing. Typically, five or six specimen-containers, each bearing encoded patient and test information in the form of a bar code or the like, are supported for aspiration by a single rack or cassette. The rack serves to align and equally space the containers to simplify the required movement of the instrument's aspiration probe in order to gain access to the interior of each container. In some instruments, the aspiration probe is located within the interior of the instrument housing; in such instruments, an integral specimen-transport system within the instrument is used to present the specimen-container racks to the probe for aspiration. In other instruments, the aspiration probe is movably-mounted on the exterior of the instrument housing; with such instruments, an external specimen-transport device or module is used to present specimen-containers to a location that accommodates the allowed movement of the aspiration probe outside the instrument housing.

U.S. Pat. No. 5,720,377, filed in the names of Lapeus et al., discloses a specimen-transport module of the type noted above. The module operates to present individual racks of specimen-containers to an externally-accessible aspiration probe of an associated clinical instrument. The module generally comprises three interrelated trays, viz., (a) an elongated input tray that is adapted to receive and temporarily store a linear queue of specimen-container racks, (b) a movably-mounted process tray that is adapted to receive racks of specimen-containers, one at a time, from the input tray and to present them to a location for specimen-aspiration and testing, and (c) an elongated output tray that is adapted to receive processed racks one at a time from the process tray and to temporarily store such racks in a linear output queue for subsequent retrieval. The input and output trays are linearly aligned, end-to-end, and each tray is provided with linear guides that interact with features on the racks to align the received racks to form the respective linear queues. The process tray is positioned adjacent to the input and output trays and extends parallel to these trays. Each of the racks comprising the input queue is forwardly advanced over the rack-supporting surface of the input tray by a magnetic transport system that underlies the input tray. The input tray is made of a nonmagnetic material (in this case, aluminum), and each specimen-container rack carries one or more magnetically-attractive members in its base portion. The magnetic transport system that underlies the tray comprises a pair of parallel conveyor belts, each carrying a plurality of permanent magnets at equally spaced locations. The belts are trained about spaced pulleys, and one reach of each of the belts is closely spaced from the underside of the input tray and extends in a direction parallel to the linear guides. As the belts are driven along their respective endless paths, the respective magnetic field of one or more of the permanent magnets carried by the belts passes through the input tray and magnetically couples with the magnetically-attractive member(s) of one or more of the racks. Thus, as the belt moves under the input tray, the magnetically coupled racks atop the tray are pulled along the linear path defined by the guides to a location where the foremost rack in the queue can be acted upon by a second conveyance of the transport system. The latter operates independently of the magnetic drive system to physically engage and push each rack from the input queue into an awaiting slot of the movably-mounted process tray. Upon presenting a rack of containers to the associated clinical instrument for processing, the process tray slides forward to a location where the processed rack can be acted upon by a third conveyance which operates to physically push the rack out of the process tray and onto the output tray, where the processed racks are guided to form the linear output queue. A fourth conveyance then operates to physically push the output queue of racks over the output tray surface to an off-lading position.

As noted in the above patent, the use of magnetic forces to advance specimen-container racks within a specimen-transport module affords certain advantages over the mechanical schemes that are commonly used to physically engage and push or pull a rack along a desired path. Since the drive mechanism for magnetically advancing racks is located below the input tray and within the housing of the transport system, its moving parts are totally isolated from the user environment and, hence, pose no potential safety hazards to the user. Moreover, since the surface of the input tray over which the specimen-container racks is moved by the magnetic transport system is plane and featureless, liquid spills, dust and dirt can be removed with relative ease. While the magnetic transport system disclosed in the above patent affords these advantages, the disclosed system can operate only to advance specimen-container racks along a linear path, e.g., that found in the transport module's input buffer; thus, its utility is substantially limited. Further, since the permanent magnets are supported by flexible endless belts, each being supported only by a pair of spaced pulleys, any tendency for the belts to sag between the pulleys will change the displacement between the magnets and the magnetically-attractive members of the racks, thereby causing an undesirable variation in the attractive force between these elements.

SUMMARY OF THE INVENTION

In view of the foregoing discussion, an object of this invention is to provide a magnetic transport system that is adapted to transport specimen-container racks in mutually-perpendicular directions atop a non-magnetic plate within a specimen-transport apparatus.

Another object of this invention is to provide a two-dimensional magnetic transport system that is capable of satisfying not only the specimen presentation needs of an individual clinical instrument with which it is directly associated, but also the specimen transport needs of a multi-instrument workcell in which specimens must be transferred between individual instruments of the workcell for testing and/or processing.

The magnetic transport system of the invention basically comprises a pair of independent, bi-directional, linear drive mechanisms, one drive mechanism serving to support the other for linear movement. The supporting drive mechanism operates to selectively advance the supported drive mechanism along a first linear path below a non-magnetic planar plate on which specimen-container racks are positioned. The supported drive mechanism, in turn, operates to selectively advance a magnetic field-producing device, preferably a plurality of permanent magnets, along a second linear path extending perpendicular to the first path and closely spaced from the bottom side of the rack-supporting plate. By controlling the linear movements of the respective drive mechanisms, the position of the magnetic field-producing device is adjustable in the X/Y (horizontal) plane. Each of the racks carries in its base portion a pair of magnetically-attractive members which become magnetically coupled to the magnetic field-producing device moving below the non-magnetic rack-support plate. During the X/Y movement of the magnetic field-producing device, the magnetically-coupled rack follows along atop its support surface. Preferably, each of the drive mechanisms is supported for linear movement along a rigid shaft or rail. By this arrangement, the spacing between the bottom of the racks and the magnetic field-producing device will remain substantially constant throughout the X/Y movement of the device, as will the magnetic force between these elements.

Being able to magnetically transport specimen container-racks over a supporting surface in mutually perpendicular directions, the specimen-transport system of the invention is much more versatile in its applications than previous systems allowing but a single degree of movement. Thus, in addition to being useful in transporting racks within the input and output buffers of specimen-transport modules, the specimen-transport system of the invention can advance a rack to and from any location in a plane bounded only by the extent of travel afforded by each of the stacked linear drive systems.

The invention and its various aspects and advantages will be better understood from the ensuing detailed description of preferred embodiments, reference being made to the accompanying drawings in which like reference characters denote like parts or components.

DETAILED DESCRIPTION OF PREFERRED EMBODIMENTS

The magnetic specimen-transport system of the invention is disclosed herein as being embodied in a stand-alone specimen-transport module described in the above-referenced U.S. application Ser. No. 10/794,702, entitled "Specimen-Transport Module for a Multi-Instrument Clinical Workcell." It will be appreciated, however, that the invention is also useful in stand-alone clinical instruments in which the specimen-transport system is an integral part of the instrument, rather than an accessory to the instrument.

Figure 1:
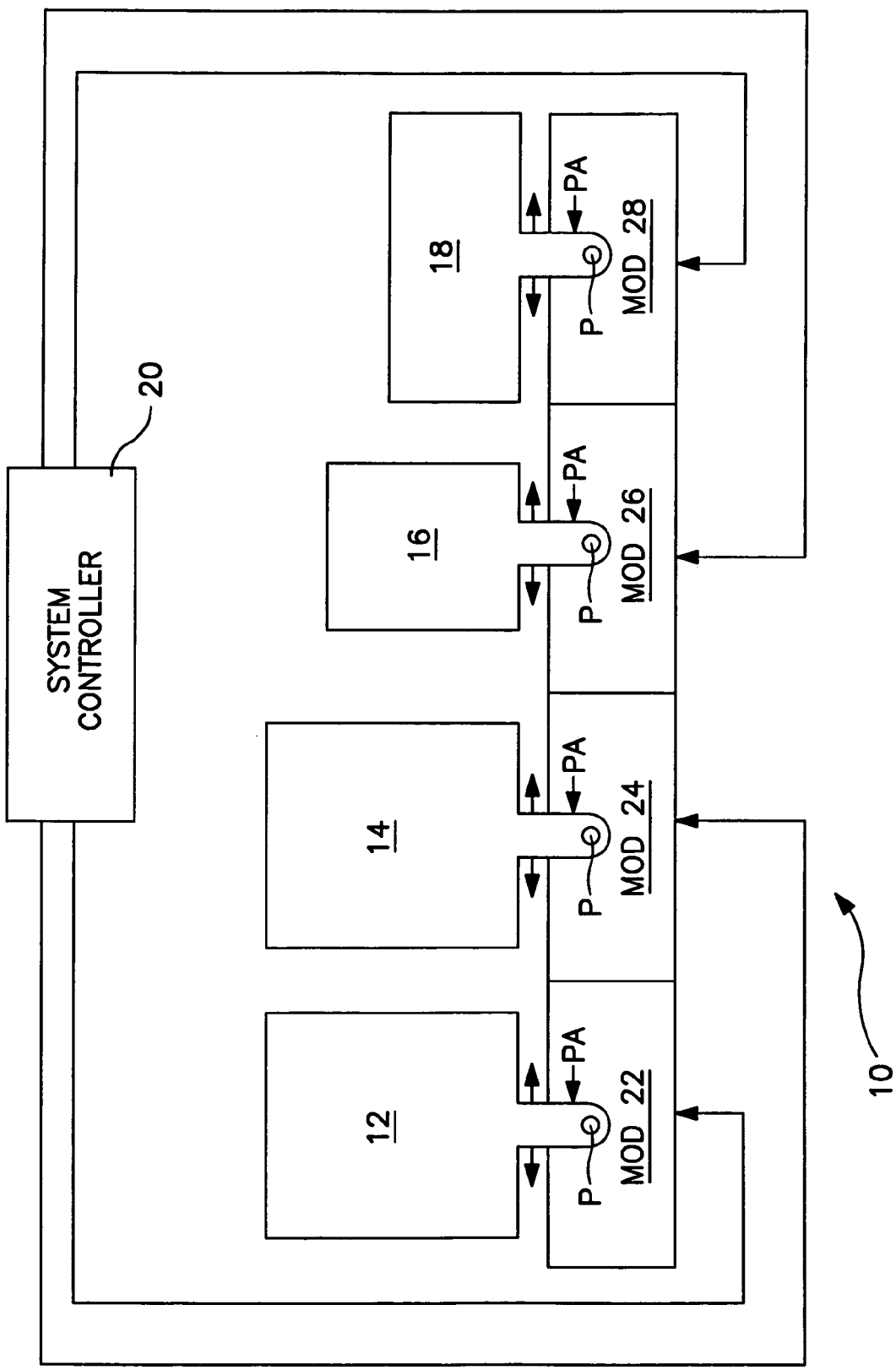
FIG. 1 is a schematic illustration of a multi-instrument clinical workcell in which the present invention is especially useful.

Referring now to the drawings, FIG. 1 schematically illustrates a multi-instrument workcell 10 that is adapted to analyze and/or otherwise process a whole blood specimen presented to it. Each of such specimens is contained by a test tube or other container C that is supported, together with additional containers, in a generally upright orientation and in a linear array, by a specimen-container rack R (shown in FIG. 10). In the workcell shown in FIG. 1, four separate clinical instruments 12, 14, 16 and 18, operate under the control of a common, microprocessor-based, system controller 20. Instruments 12 and 14 may be, for example, hematology instruments that operate, in a conventional manner, to differentiate and count the constituent blood cells of the whole blood specimen on the basis of DC volume, RF-conductivity and/or light scatter measurements made on each cell as it passes through the sensing aperture of a conventional flow cell. Instrument 14 may be, for example, a fluorescence flow cytometer that operates, in a conventional manner, to differentiate cell types based on the combination of fluorescence measurements and either light-scatter, DC volume or RF conductivity measurements made on each cell as it is made to pass through the sensing zone of an optical flow cell. Instrument 18 may be, for example, a slide-maker/slide-stainer device that produces and subsequently stains a smear of specimen on a microscope slide that can be subsequently analyzed under a microscope. While these clinical instruments can substantially differ in both the tasks they perform and in their mechanical make-up, each instrument has in common a movably-mounted aspiration probe assembly PA that is mounted on the exterior of the instrument housing and, hence, is accessible for the presentation of specimen containers ready for aspiration. The probe assemblies are mounted for movement both vertically (into the plane of the drawing) so as to enter a specimen-container presented to it in order to aspirate a small volume of the contained specimen for processing, and laterally (as indicated by the arrows) so as to enter any one of the specimen-containers supported by a specimen-container rack.

Workcell 10 further comprises a plurality of identical specimen-transporting modules (MOD 22, MOD 24, MOD 26 and MOD 28), one being operatively connected to, or otherwise associated with, each of the four clinical instruments 12, 14, 16 and 18. Each of the specimen-transporting modules provides at least two functions: Firstly, it functions to satisfy all specimen-presentation needs of the instrument with which it is directly associated, i.e., it functions (i) to receive multiple racks of specimen containers manually delivered to an input buffer of the module, (ii) to selectively transport such racks from the input buffer to a specimen-aspiration station at which all of the specimen containers of a given rack are accessible to the aspiration probe assembly of the associated instrument, and (iii) to deliver a rack to an output buffer following a desired specimen aspiration from all or selected ones of the containers in the rack. Upon being delivered to the output buffer, a rack, may be advanced to an off-loading position where it can be manually removed from the module or, alternatively, it may be returned to the specimen-aspiration station for reflex or repeat testing, as may be the case if a first test result indicates that a second aspiration of a given sample is required, or if a first test result is clearly erroneous. Secondly, each of the specimen-transporting modules functions to transfer racks of specimen-containers between adjacent modules associated with other clinical instruments, thereby enabling all instruments of the workcell to process a given specimen without need for any independent specimen-transfer mechanism, e.g., a robotic arm, or a conveyor system. To provide the latter function, each of the modules is rigidly connected to adjacent modules, thus enabling the modules to pass specimens back and forth, as described below with particular reference to FIG. 6. Preferably, each of the specimen-transport modules further provides a third function, namely, that of preparing a specimen for subsequent processing. Such sample-preparation is achieved by a specimen-mixing device that operates to repeatedly invert a specimen-container rack presented to it, thereby repeatedly inverting and mixing the contained specimens. Further structural details of the specimen-transporting modules are described in the above-referenced U.S. patent application Ser. No. 10/794,702.

Figure 2:
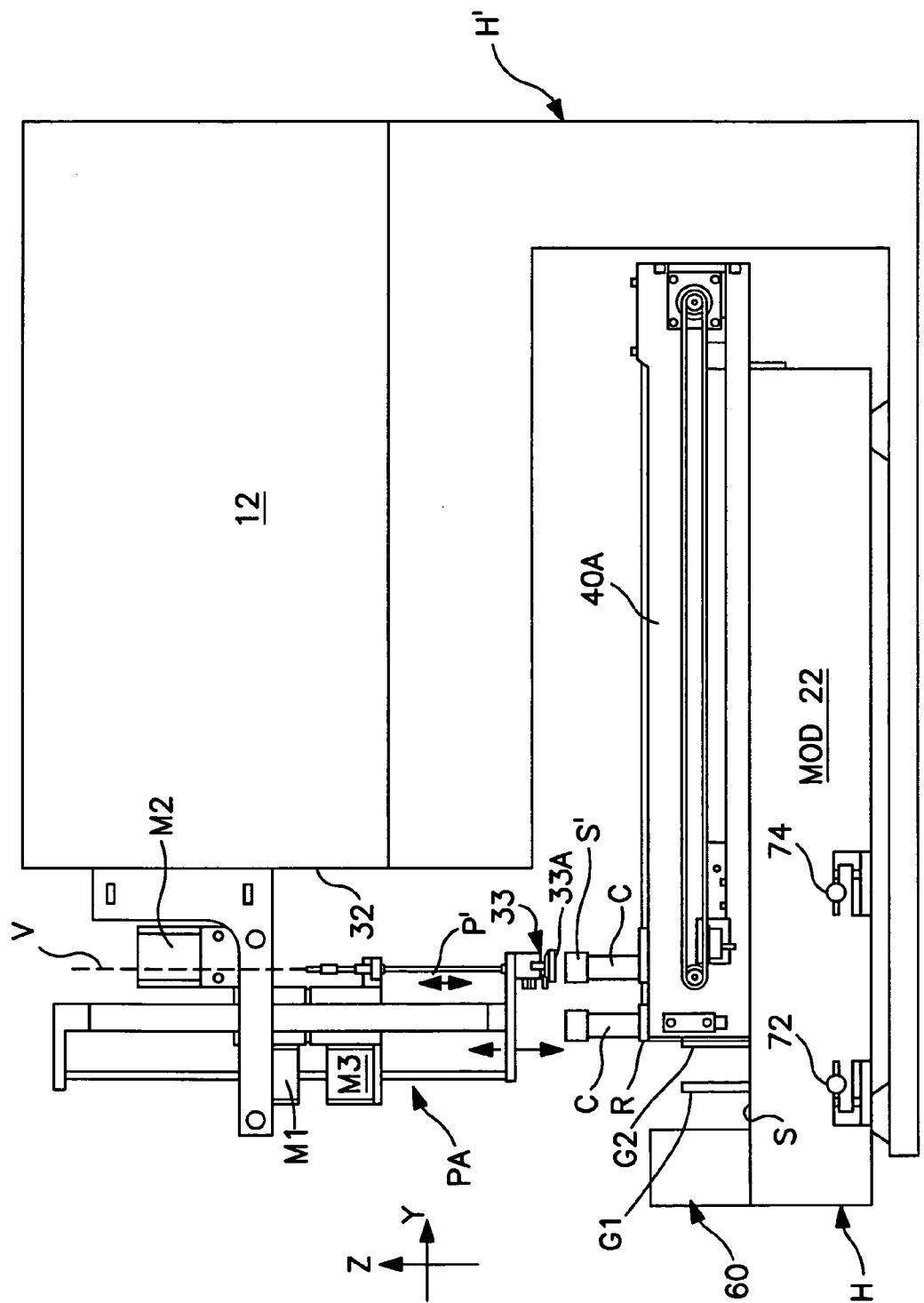
FIG. 2 is a side illustration of a specimen-transport module in combination with a clinical instrument.

In the side illustration of FIG. 2, the relationship between a specimen-transport module, e.g., MOD 22, and its associated clinical instrument, in this case instrument 12, is shown. To minimize the space requirements of the module/instrument combination, the instrument is designed to enable a major portion of the module housing H to underlie the main housing H' of the clinical instrument. The instrument's aspiration probe assembly PA extends forwardly of the front wall 32 of the instrument housing, and the specimen-transport module operates to selectively support a specimen-container rack R in an aspiration position 50 (shown in FIG. 3) so that the specimen-containers C supported by the rack are arranged in a common vertical plane V that coincides with the plane of vertical movement of the aspiration probe P'. The structural and operational details of the probe assembly are well understood and form no part of the invention. Briefly, however, movement of the probe assembly is controlled by three stepper motors, M1, M2 and M3, that operate under the control of the system controller 20. Stepper motor M1 operates to move the aspiration probe and a stripper mechanism 33 in a vertical plane, i.e., along the Z coordinate in FIG. 2, whereby the bottom surface 33A of the stripper mechanism can be moved downwardly into contact with the top surface of a rubber seal S' that encloses the top of the specimen container containing the sample to be aspirated. Stepper motor M3 then operates to control the vertical position of the aspiration probe P' of the probe assembly, whereby the probe tip can be driven downwardly so as to puncture the seal S' and enter the container for the purpose of aspirating a volume of specimen from within the container. Following specimen aspiration, motor M3 then operates to raise the aspiration probe out of the container. As the probe moves upwardly, the stripper mechanism 33 is held stationary and in contact with the seal S', thereby resisting the tendency of the upwardly-moving aspiration probe to lift the container out of the rack as a result of the frictional forces between the container seal and the aspiration probe. After the probe tip clears the top of the container seal, motor M1 operates to lift both the stripper mechanism and the aspiration probe to a vertical position in which the stripper mechanism is well clear of the container seal. The third stepper motor M2 operates to selectively advance the probe assembly laterally, i.e., in a horizontal plane, whereby the aspiration probe may access any one of the specimen containers supported by a rack located at an specimen-aspiration station 50, shown in FIG. 3.

Figure 3:
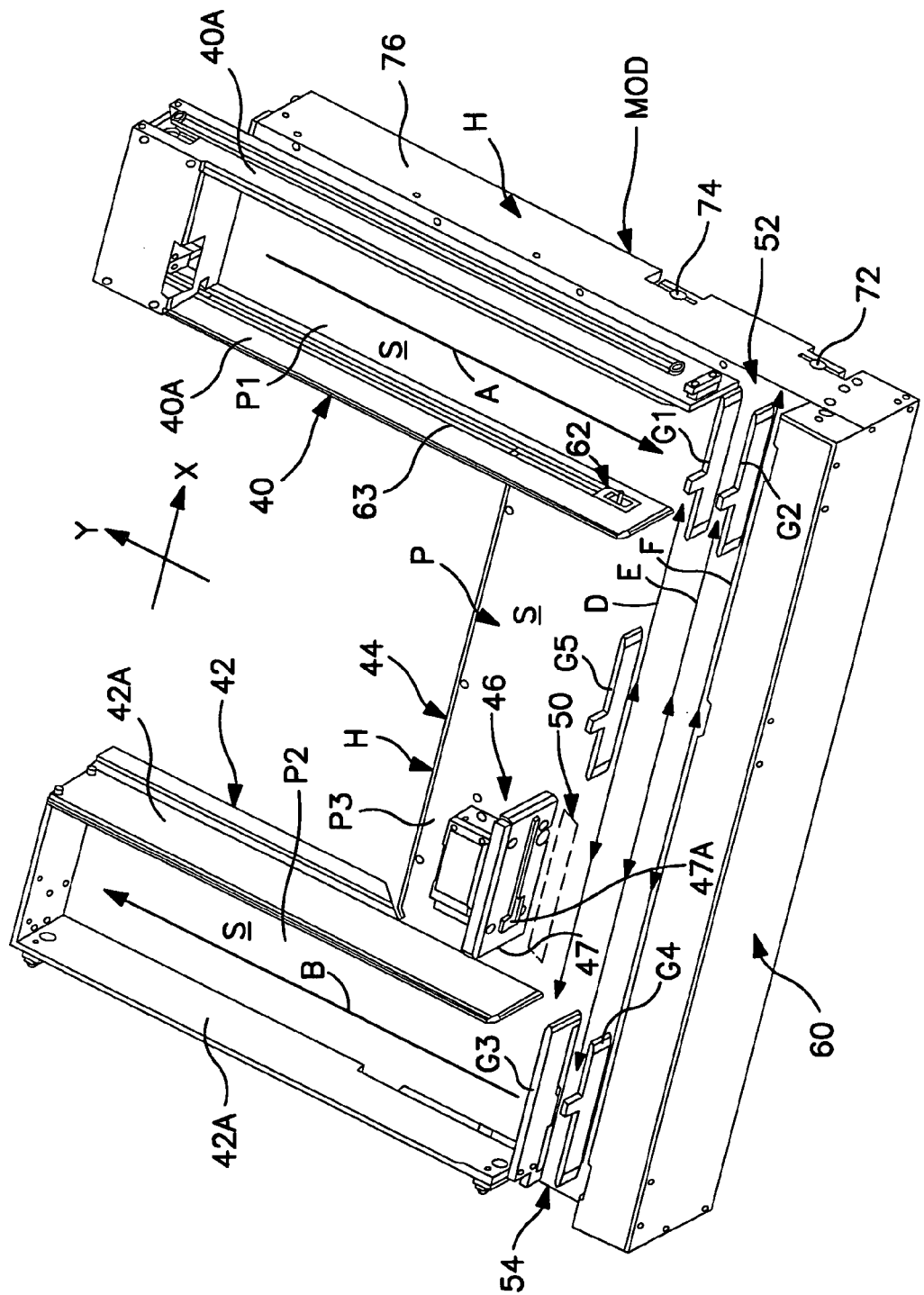
FIG. 3 is a perspective illustration of a specimen-transport module embodying the present invention.
Figure 4:
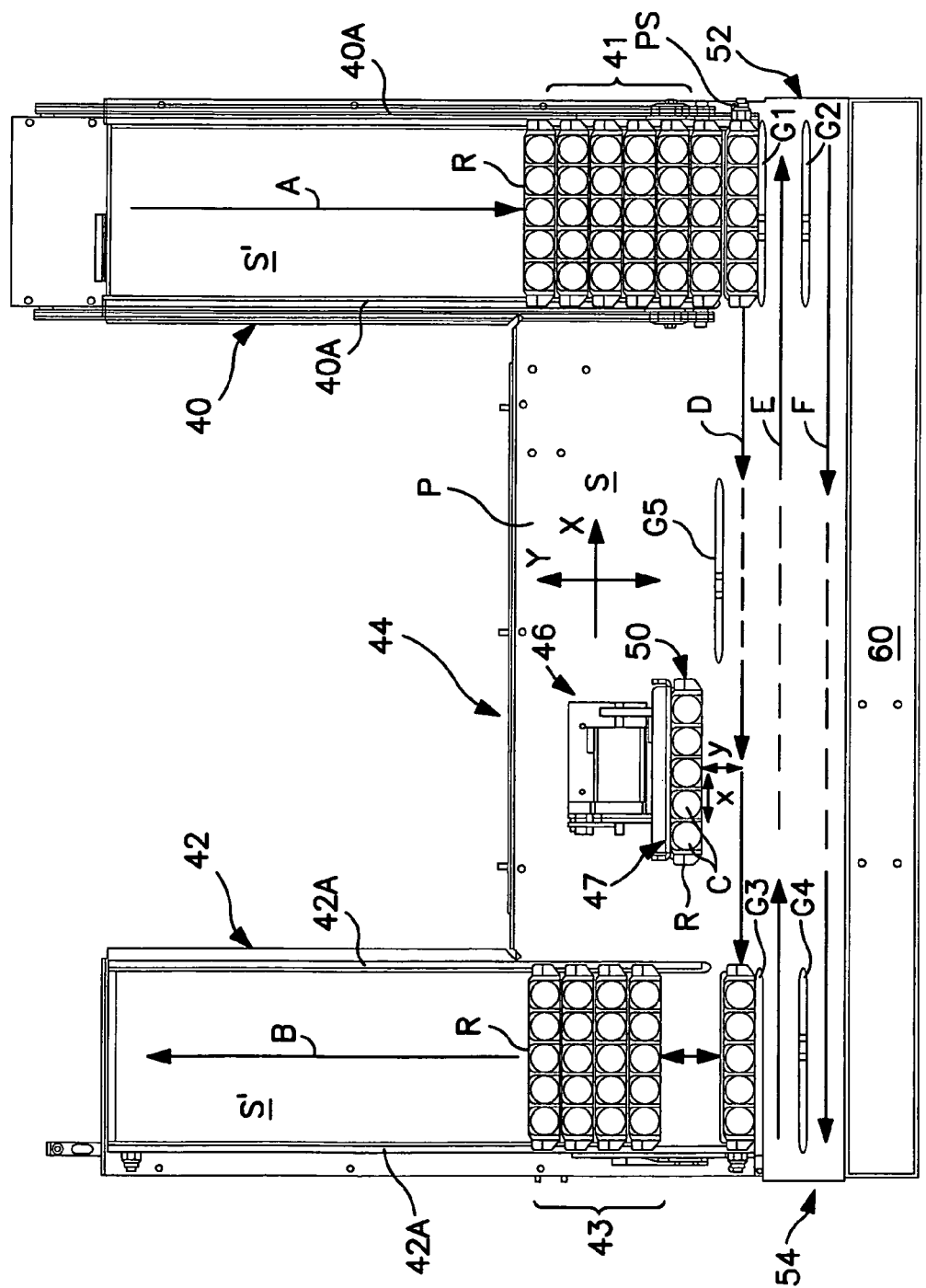
FIGS. 4 and 5 are top and front views, respectively, of the apparatus shown in FIG. 3, further illustrating the spatial positions of various specimen-container racks transported by such apparatus.
Figure 5:
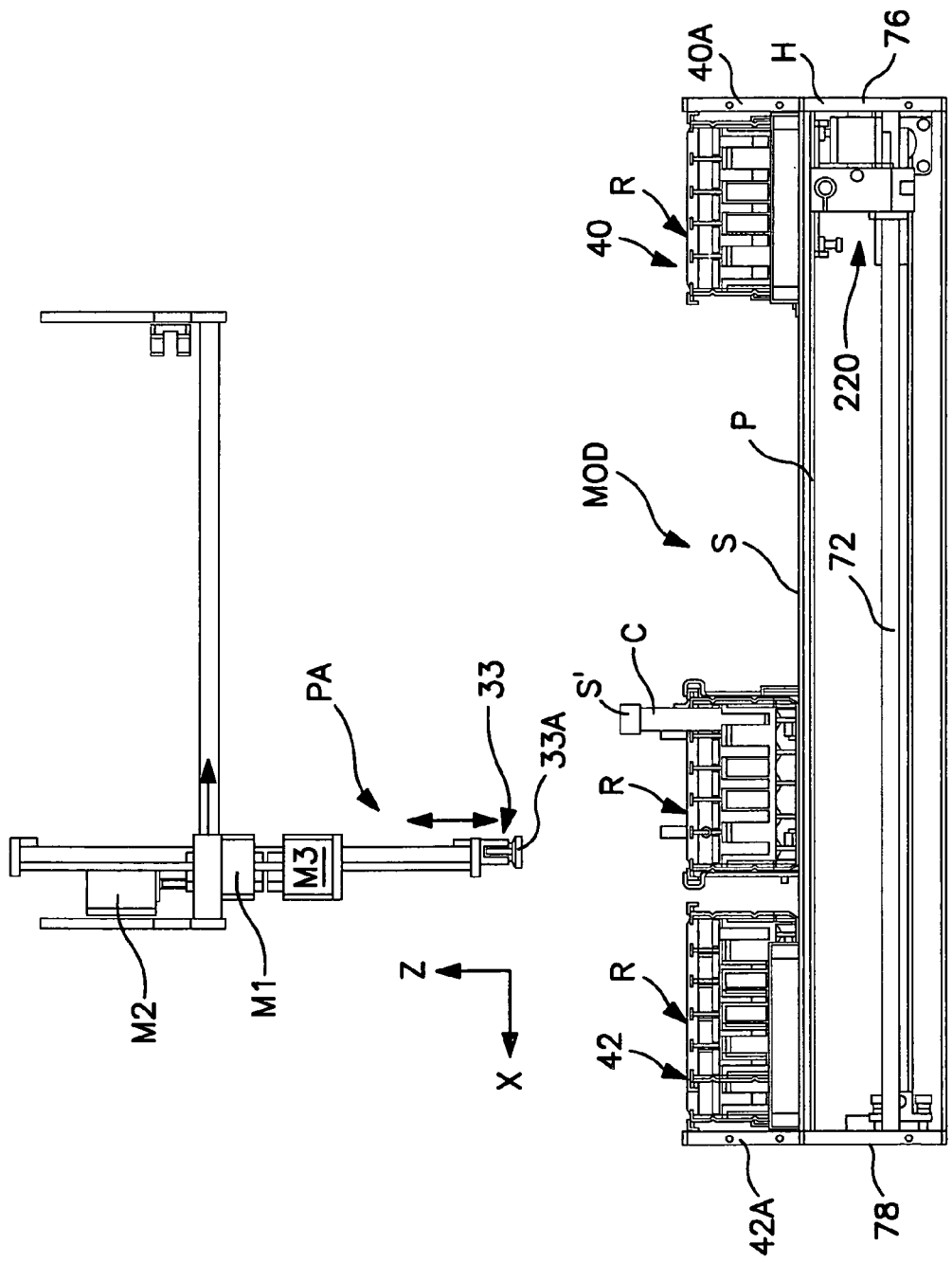
Figure 10:
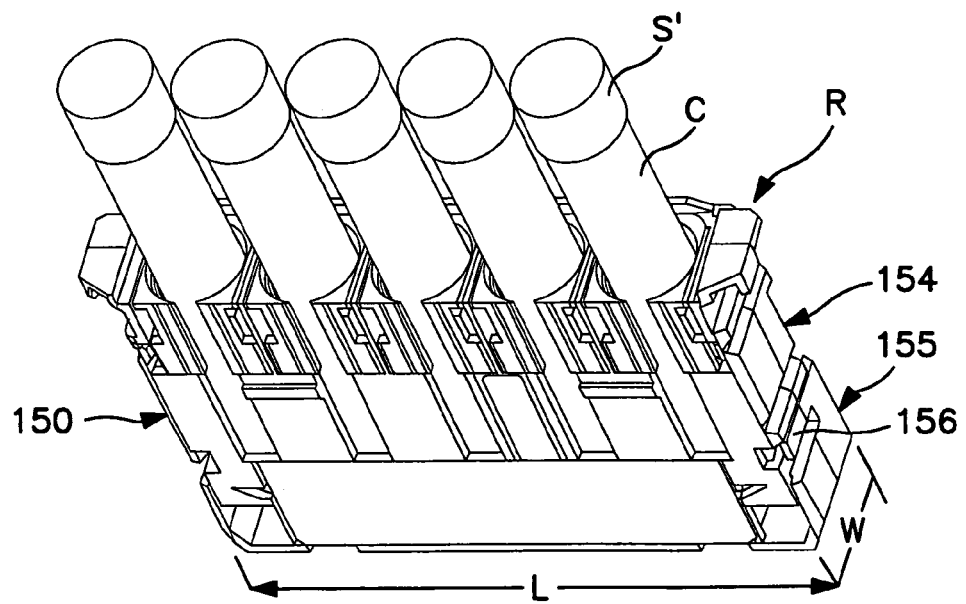
FIG. 10 is a perspective view of a specimen-container rack containing a plurality of specimen containers.

Referring additionally to FIGS. 3 and 4, each of the specimen-transport modules shown in FIG. 1 comprises a U-shaped housing H that defines (i) an input buffer 40 that is adapted to receive and support up to, say, twenty of the specimen-container racks R of the type shown in FIG. 10; (ii) an output buffer 42 in which racks of specimen-containers are accumulated after their respective specimens have been processed; and (iii) a specimen-processing section 44 through which individual racks of specimen-containers are advanced to appropriately position the racks for specimen-aspiration and/or mixing, or for transfer to an adjacent module. While racks within the input and output buffers are constrained to move along linear paths, respectively indicated by arrows A and B in FIG. 3, racks passing through the processing section 44 are not so constrained. In fact, they are required to move along various mutually perpendicular paths in the X/Y plane (as indicated by the X/Y coordinates in FIGS. 3 and 4) in order for the module to provide the specimen presentation and transfer functions noted above.

In presenting a rack of specimen-containers to the aspiration station 50 for processing, a rack will be conveyed forwardly along the specimen-processing path D which extends parallel to the X-coordinate. Upon reaching a position approximately opposite the specimen-aspiration station 50, the rack is moved rearwardly, i.e., towards the rear of the module in the Y direction, until it contacts a mounting plate 47 associated with a specimen-mixing device 46. As illustrated in FIG. 4, the distance y traveled in the Y-direction is somewhat greater than the width W of a rack, thereby enabling another rack to pass along path D without interference from a rack positioned adjacent the mounting plate 47. Upon contacting the plate 47, the rack is moved forwardly again, in the X-direction, by a short distance x. In moving as described, the rack is precisely located at the aspiration station 50 and the containers are then in a position to be accessed by the aspiration probe assembly of the associated clinical instrument. Moreover, during the short movement of the rack in the X-direction, the rack becomes securely mounted on the mounting plate 47 via a tongue-and-groove, described below. The mounting plate 47 of the mixing device is rotatably mounted and, as it rotates, it acts to lift and invert a rack secured to it, thereby mixing the specimens within the containers. Preferably, specimen-mixing is carried out immediately before each specimen is aspirated from a container, thus assuring a homogeneous specimen. After aspirating one or all of the specimens in a rack, the rack is moved backwards along the same X/Y paths as described, thereby releasing the rack from the mounting plate 47 and returning the rack to the specimen-transport path D. The rack is then transported further along path D in the X-direction until it reaches a position opposite the output buffer 42. The rack is then moved into the output buffer by moving it rearwardly on surface S, in the Y-direction. In the event the test results from the rack last entered into the output buffer indicate that a test needs repeating, the rack is retrieved from the output buffer and is moved in the reverse direction along path D to a position upstream of the aspiration and mixing stations to await the completion of the processing of a rack then present at the aspiration station. After such processing is completed and the aspiration/mixing station 50 is vacated, the rack requiring reprocessing is again advanced to station 50 for processing.

In the event that tests need to be performed on a given specimen by another instrument in the workcell, a rack containing such specimen will be transported to either of the transport paths E or F which lead to specimen transfer stations 52 and 54 located on opposite sides of the module. At these stations, a rack can be transferred to a corresponding transfer station of an adjacent specimen-transport module in a multi-instrument workcell. The manner in which a rack is transferred from one module to another is described below with reference to FIG. 6.

Figure 6:
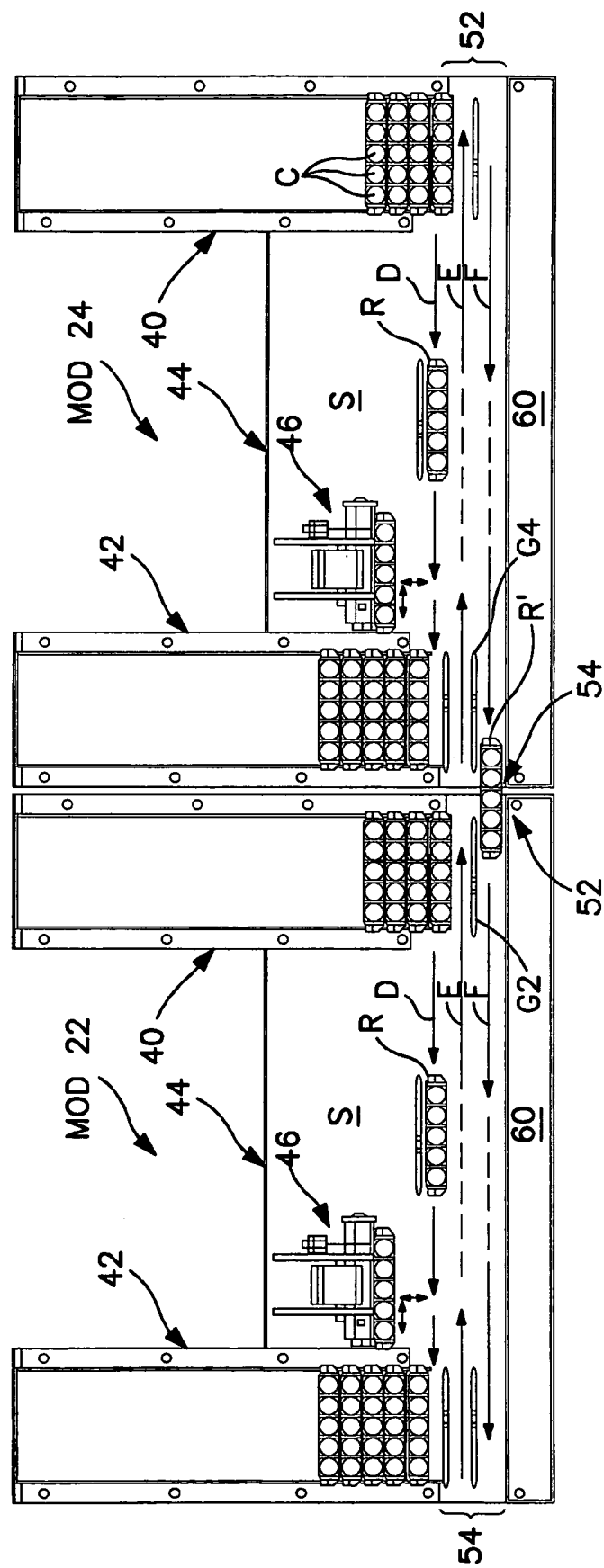
FIG. 6 is a top plan view of two adjacent specimen-transport modules of a multi-instrument workcell illustrating the transfer of a specimen-container rack from one module to another.

Referring to FIG. 6, two adjacent specimen transport modules, MOD 22 and MOD 24, are depicted during the process of transferring a specimen-container rack R' from MOD 24 to MOD 22. As shown, rack R' has been transported along path F to the rack-transfer station 54 of MOD 24, and to the corresponding path F of rack-transfer station 52 of MOD 22. As explained below, rack R' has been advanced to the "spanning" position shown by an X/Y magnetic transport system of MOD 24 that underlies the module's upper surface. Such a transport system operates to magnetically engage a rack at two locations in the rack's base portion where two magnetically-attractive members are mounted. Such members are spaced apart at opposite ends of the rack. To advance a rack to the position shown, i.e., where the rack spans two adjacent modules, a rack is first advanced to a position in which the rack's leading edge is approximately coincident with the edge of the module and the rack's side is adjacent guide member G4. The magnetic transport mechanism is then decoupled from the rack by moving the transport mechanism in the Y direction, towards guide member G3. Since the rack cannot follow the magnetic transport mechanism in this direction due to its engagement with guide G4, the magnetic coupling between the rack and transport mechanism will be overcome, and the rack will remain at the edge of the module. Thereafter, the magnetic transport mechanism will be repositioned to magnetically engage only one of the two magnetically attractive members carried by the rack, i.e., the member more inboard from the module edge. The transport mechanism will then operate to advance the rack off the edge of MOD 24 and into the transfer station of the adjacent module MOD 22. The magnetic drive system of MOD 22 is then moved to a position in which it magnetically engages the rack at rack-transfer station 52 and transports it over the surface S of MOD 22 as required. It will be appreciated that rack-transfer between the specimen-transport modules can be effected on either of paths E or F, as determined by the system controller 20, which controls the traffic pattern of the racks throughout the module (and workcell). Preferably, however, one path is used to transfer racks in one direction, and the other path is used to transfer racks in the opposite direction. Not shown in the drawings is a pair of photoelectric sensors that detect the presence of a rack at each of the rack-transfer stations. When a rack that is to be transferred to another specimen-transport module is transported to either of the opposite end of paths E or F of a rack-transferring module, its presence is sensed by a sensor at the rack-transfer station of the transferring module. When a rack is also detected at the rack-transfer station by the sensor of the rack-receiving module, the rack is now in a position to be acted upon by the X/Y rack-transport mechanism of the receiving module. The system controller acts on the output of these sensors to send the X/Y transport mechanism of the receiving module to further transport the rack therein.

Referring again to FIG. 3, the specimen-transport module housing H comprises a U-shaped top plate P comprising opposing leg portions P1 and P2, and an interconnecting base portion P3. The opposing leg portions P1 and P2 serve to support specimen-container racks in the input and output buffers 40 and 42. The base portion P3 serves to support racks for the above-described two-dimensional (X/Y) movement in the processing section 44. Preferably, plate P is a non-magnetic stainless steel plate about 1.5 mm. in thickness. Its top surface is smooth, plane and featureless, and it is this surface that supports and slidingly engages the bottom surface of the specimen-container racks as they are moved along the various X-and Y-extending paths within the module. Each of the input and output buffers 40 and 42 comprises a pair of parallel side walls 40A, 42A, respectively. These walls extend upwardly from surface S and are spaced apart by a distance slightly greater than the length L of the specimen-container racks, whereby the rack may be received by the buffers and aligned as shown in FIG. 4. Two pair of upwardly-extending and parallel guides members, G1, G2, and G3, G4, are arranged on surface S at the rack-transfer stations 52 and 54 to assure that the racks are properly aligned (i.e., not skewed) on paths E and F during the transfer of racks between modules. Guide G1 further serves as a stop against which racks in the input buffer can be registered prior to being moved edgewise into the specimen-processing section along path D of the module. A fifth guide member G5 serves to properly align each rack as it approaches the specimen-aspiration station 50 along path D.

Referring to the top view of FIG. 4, individual specimen-container racks are manually loaded at a loading station within the input buffer 40, typically to the rear of the last rack in the input queue 41, i.e., the rack farthest from the front housing 60. The racks are mechanically urged forwardly along the linear path A by a pair of opposing cam-actuated pusher members 62 (shown in FIG. 3) that are selectively driven forwards and backwards in linear slots 63 formed in the buffer side walls 40A. The pusher members are mounted for movement between an extended position (as shown in FIG. 3) in which they protrude from the side walls and engage a rack from both sides as the members are driven forwardly, towards the path D, and a retracted position in which they are recessed behind the side wall to enable the pusher members to move behind the last rack in the input queue in order to advance it, and the racks in front of it, forwardly. The mechanism for advancing the racks in the input buffer is described in detail in the above-referenced application Ser. No. 10/794,702. A photo-sensor PS (e.g., a conventional photoelectric sensor that operates on the basis of a sensed reflectance signal) is mounted on top plate P at the forward end of the input buffer and serves to signal the system controller 20 when the foremost rack in the queue has reached a position adjacent to the guide member G1. Upon reaching this position, a rack is ready to be acted upon by the magnetic transport system of the invention which serves to transport racks of specimen containers through the specimen-processing section 44 of the module.

In accordance with the present invention, a magnetic transport system is provided for advancing specimen-container racks in a two-dimensional (X/Y) plane through the specimen-processing section 44 of the transport module described above. Such a system comprises a magnetic rack-transport mechanism 70 (shown in FIG. 7) that underlies the base portion P3 of the U-shaped non-magnetic plate P and operates to advance magnetically-attractive specimen-container racks positioned atop the plate. Preferably, the racks are rendered magnetically-attractive by mounting a pair of ferromagnetic members (shown in FIG. 12) in the rack's base portion at opposite ends. As explained below, mechanism 70 comprises a magnetic field-producing device, preferably in the form of a pair of permanent magnets. The magnets are carried by a "truck" which is mounted for movement in the X/Y plane beneath and in close proximity to the bottom side of plate P. The magnetic field produced by each magnet passes through the non-magnetic support plate P of the transport module and magnetically couples with the magnetically-attractive members carried in the base portion of each specimen-transport rack. The magnetic bond between the magnets and magnetically-attractive members is sufficiently strong that, as the magnet-bearing truck moves in the X/Y plane beneath plate P, a magnetically-coupled rack atop the plate's upper surface S follows along.

Figure 7:
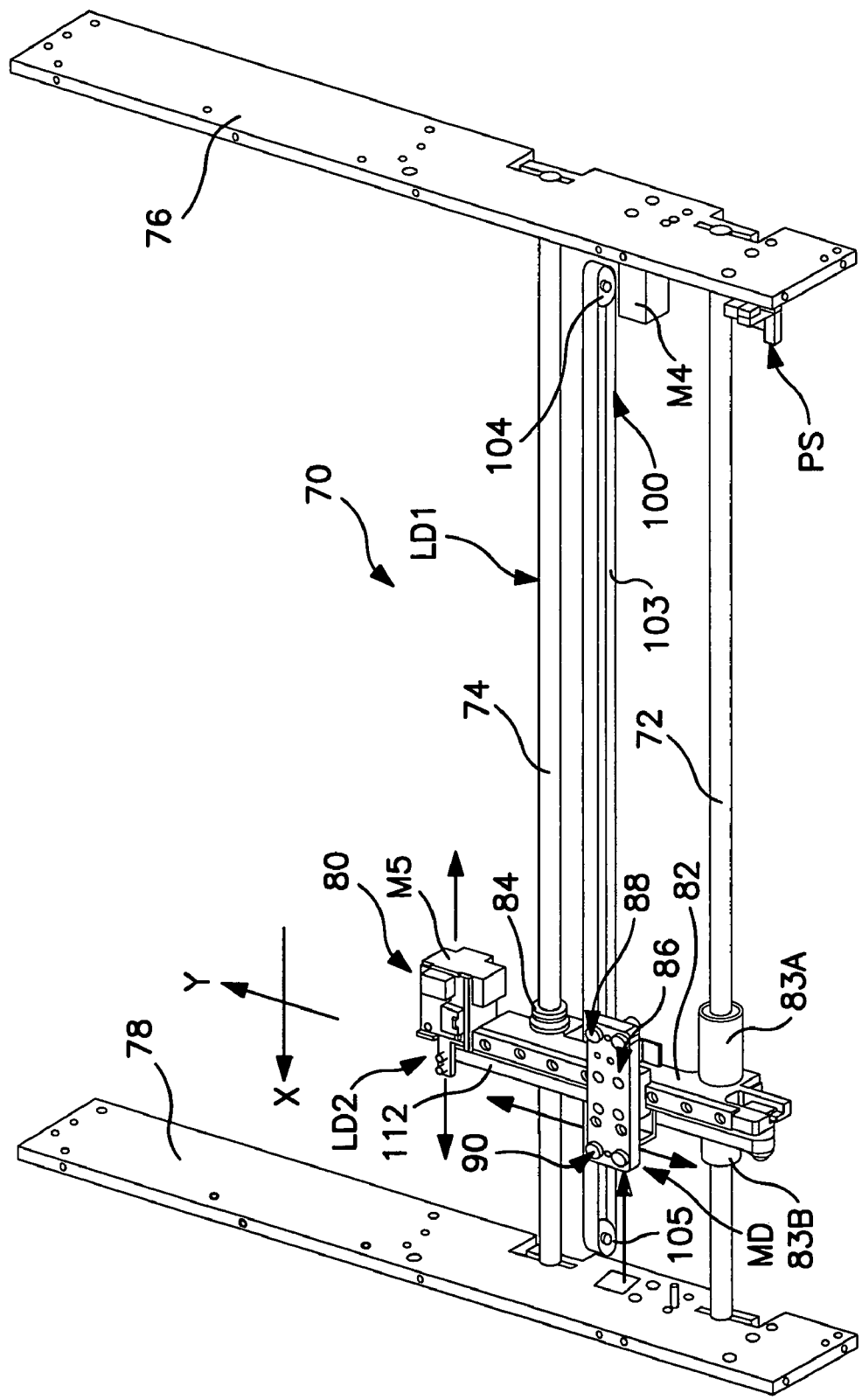
FIG. 7 is a perspective illustration of a preferred X/Y drive mechanism for controlling the X/Y position of individual specimen-container racks in the specimen-processing portion of the specimen-transport module shown in FIG. 1-6.

Referring to FIG. 7, a preferred X/Y transport mechanism 70 is shown as comprising a pair of independent, bi-directional, linear drive mechanisms LD1 and LD2. One drive mechanism (LD1) serves to support the other (LD2) for movement along a first linear path parallel to the X-coordinate. LD1 also serves to selectively advance LD2 along such path in either direction. LD2, in turn, serves to support a magnetic field-producing device MD for movement along a second linear path extending perpendicular to the first linear path, i.e., in a direction parallel to the Y-coordinate; LD2 also serves to selectively advance the magnetic field-producing device in either direction along such second linear path. The second linear path is closely spaced from a bottom surface of the non-magnetic support plate, and the magnetic field-producing device is effective to produce a magnetic field atop the non-magnetic support plate that is sufficiently strong to magnetically engage the base portion of a rack positioned atop the support plate. Thus, as the magnetic field-producing device is advanced along the second linear path by LD2, and as LD2 is advanced along the first linear path by LD1, the rack moves atop the support plate in the X/Y plane and along the mutually perpendicular paths determined by the loads of LD1 and LD2. The structural particulars of the drive mechanisms are discussed below.

Figure 8A:
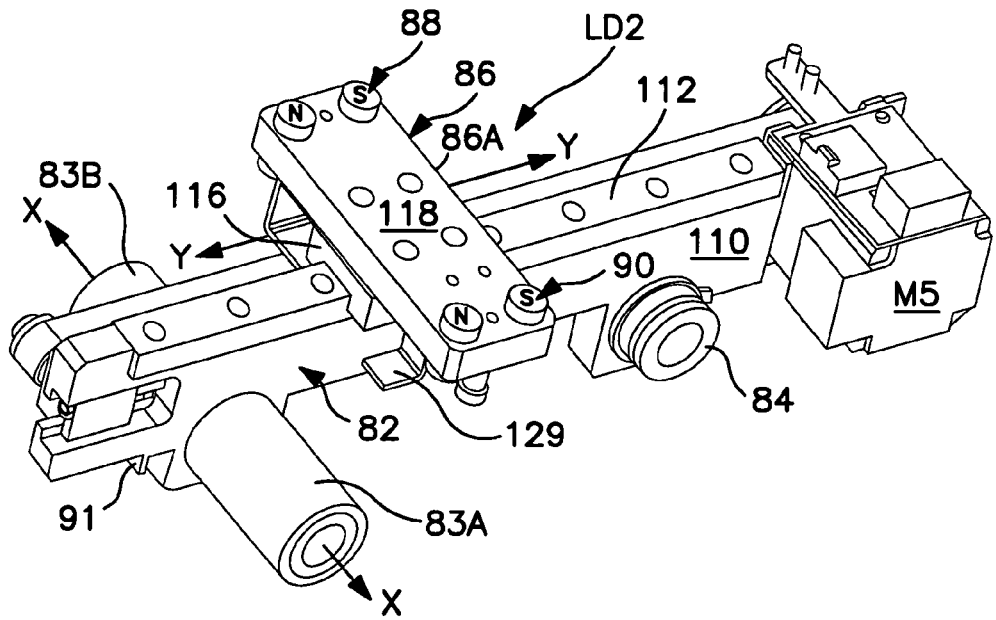
FIGS. 8A and 8B are enlarged perspective views of the Y-drive portion of the FIG. 7 apparatus.
Figure 8B:
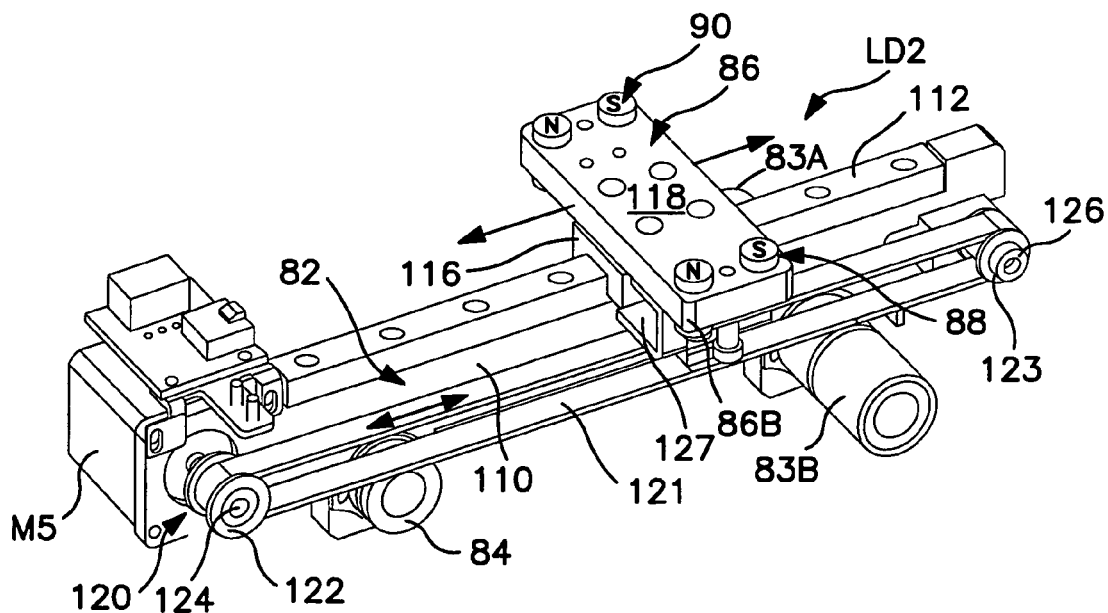

As shown in FIG. 7, linear drive mechanism LD1 comprises a pair of spaced and substantially parallel support shafts 72, 74 that are supported at their respective ends by the opposing side walls 76, 78 of the module housing H. A preferred spacing between shafts 72 and 74 is about 16 cm. As shown, shafts 72 and 74 extend parallel to the X coordinate and, together, they support the second linear drive mechanism LD2 for sliding movement parallel to the X coordinate. As best shown in FIGS. 8A and 8B, LD2 comprises an elongated housing 82 in which three sleeve bearings 83A, 83B and 84 are mounted. Bearings 83A and 83B are positioned on opposite sides of housing 82, and they are aligned to slide on shaft 72, the so-called "datum" shaft. The respective outboard edges of bearings 83A and 83B are relatively far apart, e.g., about 10 cm., to assure that the LD2 housing 82 remains perpendicular to the datum shaft at all times during its travel therealong. Bearing 84 is supported in a horizontal slot formed in housing 82, and this bearing rides along shaft 74 (the "anti-rotation" shaft) during movement of the LD2 housing in the X direction. The slot mounting enables bearing 84 to slide smoothly along the anti-rotation shaft even though the latter may not be perfectly parallel to the datum shaft; at the same time, however, the slot mounting prevents the LD2 housing from pivoting (about the datum shaft), thereby assuring that this housing remains in a horizontal (X/Y) plane at all times during movement of the truck assembly along the datum shaft. As explained below, the LD2 housing itself supports a permanent magnet-bearing truck 86 for sliding movement parallel to the Y coordinate. Preferably, truck 86 carries a pair of U-shaped magnets 88, 90 that magnetically interact and couple with a pair of magnetically-attractive members 170 (shown in FIG. 12) carried in the base portion of each specimen-container rack. As noted above, such magnetic interaction between the magnets and the magnetically-attractive members 170 is sufficiently strong to cause the specimen-container racks to slide across surface S and to follow the movement of the magnetic truck 86 beneath surface S.

As shown in FIG. 7, movement of the LD2 housing in the X direction (i.e., along shafts 72 and 74) is effected by a belt drive mechanism 100 mounted between the module housing walls 76 and 78. Drive mechanism 100 comprises an endless belt 103 that spans between a drive pulley 104 and idler pulley 105. Drive pulley 104 is rotatably driven by the drive shaft of an X-drive motor M4 mounted on housing wall 76. Motor M4 is a bi-directional stepper motor that operates under the control of the system controller 20. A tab 91 located at one end of the LD2 housing 82 is sensed by a photoelectric sensor (not shown) mounted on the module housing side wall 76 to provide a "home" position for the X-drive mechanism and a point of reference for the X-position of the magnetic truck 86.

Referring to FIGS. 8A and 8B, the LD2 housing 82 of the X/Y magnetic drive mechanism 70 comprises an elongated bar 110 in which the above-noted sleeve bearings 83A, 83B and 94 are mounted. Bar 110 supports a linear rail 112 along its uppermost surface. Rail 112 extends in a direction perpendicular to the respective longitudinal axes of the sleeve bearings; thus, when the sleeve bearings are mounted on their respective shafts, rail 112 extends parallel to the Y coordinate. Rail 112, in turn, slidably supports the above-noted permanent magnet-bearing truck 86. The latter comprises a channel-shaped member 116 which is adapted to slide along rail 112. Member 116 is rigidly connected to a non-magnetic plate 118 on which the permanent magnets 88 and 90 are mounted, as described below. As best shown in FIG. 8B, plate 118 is selectively driven along rail 112 by a second belt drive mechanism 120. The latter comprises an endless belt 121, a pair of pulleys 122, 123, and a bi-directional stepper motor M5 (the Y-drive motor) which communicates with and is controlled by the system controller 20 via a flex cable, not shown. Pulley 122 is rotatably driven by the drive shaft 124 of motor M5, and idler pulley 123 is mounted for rotation on a fixed shaft 126 extending from bar member 110. The respective axes of shafts 124 and 126 extend parallel to the X coordinate. Belt 121 is trained about the drive and idler pulleys as shown, and it is operatively connected to the magnetic truck assembly 94 by a bracket 127, best shown in FIG. 9. Thus, it will be appreciated that as the drive shaft of stepper motor M5 rotates, belt 121 advances over pulleys 123 and 123 and, owing to the connection of the belt and the magnetic truck assembly 94, the position of the permanent magnets carried by plate 118 in the Y direction is determined by the axial position of the stepper motor drive shaft. A flag member 129 depending from the bottom surface of plate 118 is sensed by a photoelectric sensor PS (shown in FIG. 7) mounted on side wall 76 of housing H to determine the "home" position of the Y-drive mechanism, and thus provides a point of reference for the Y position of the magnetic truck. The X and Y sensors on the housing frame are positioned such that X home position of the truck is sensed first, and then its Y home position is sensed.

Figure 9:
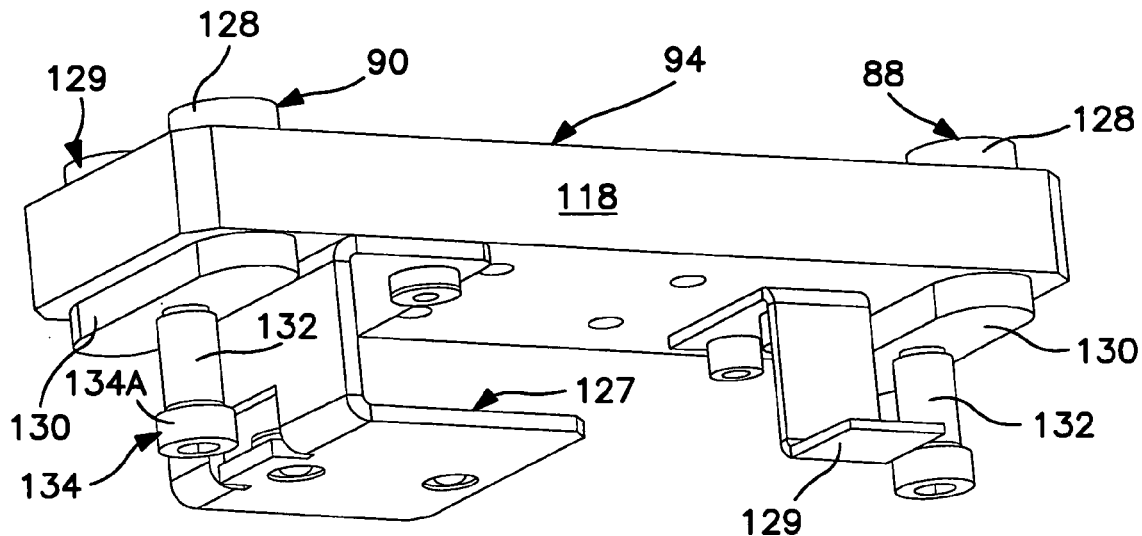
FIG. 9 is an enlarged bottom perspective view of the magnetic X/Y truck used in the FIG. 7 apparatus to magnetically engage a specimen-container rack.

Still referring to FIG. 9, each of the permanent magnets 88 and 90 comprises a pair of cylindrical bar magnets 128, 129, that are connected by a flux bridge 130. The bar magnets are received by cylindrical bore holes formed in plate 118, and they are positioned such that opposite magnetic poles (north/south) extend above the plate surface. The permanent magnets are biased upwardly by a spring 132 that surrounds a shoulder screw 134, threaded into the base of plate 118 and extending downwardly, through a clearance hole formed in the flux bridge. One end of the coil springs is supported by the bolt head 134A, and the opposite end of the spring engages the flux bridge and thereby urges the flux bridge into contact with the underside of plate 118. Preferably, each of the bar magnets has a diameter of about 9.5 mm., and magnets are spaced apart by about 19 mm., center-to-center. The length of each magnet is such as to protrude about 3 mm. above the plate 118 when the flux bridge contacts the underside of the plate. Preferably, each of the magnets comprises neodymium-doped iron. The flux bridge is made of iron and is about 3 mm. in thickness. Preferably, the X/Y drive system 70 is positioned so that a spacing of about 1 mm. is provided between the top of the bar magnets and the bottom of the rack-support plate P.

In the X/Y drive mechanism described above, it should be noted that the spacing between the permanent magnets carried by the magnetic truck 86 and the bottom surface of plate P can be maintained substantially constant throughout the X/Y movement of the truck. This attribute of the system results from the rigid mounting scheme, utilizing rigid shafts or rods 72, 74 and the rail 112, for supporting the truck as it moves. Contrast this mounting scheme with the prior art scheme for moving magnets in a linear magnetic transport system drive where flexible belts support the magnets for "linear" movement. Thus, the system described herein provides a substantially uniform magnetic force between the racks and the magnetic field-producing device no matter where the device is in the X/Y plane.

Referring now to FIG. 10, a preferred specimen-container rack R adapted for use with the magnetic specimen-transport apparatus described above is shown as comprising a housing 150 that defines plural (in this case five) compartments 152 for receiving a like plurality of specimen containers C. The particular rack shown is the subject matter of the above-referenced U.S. application Ser. No. 10/794,685, and entitled "Specimen-Container Rack for Automated Clinical Instrument."

Figure 11A:
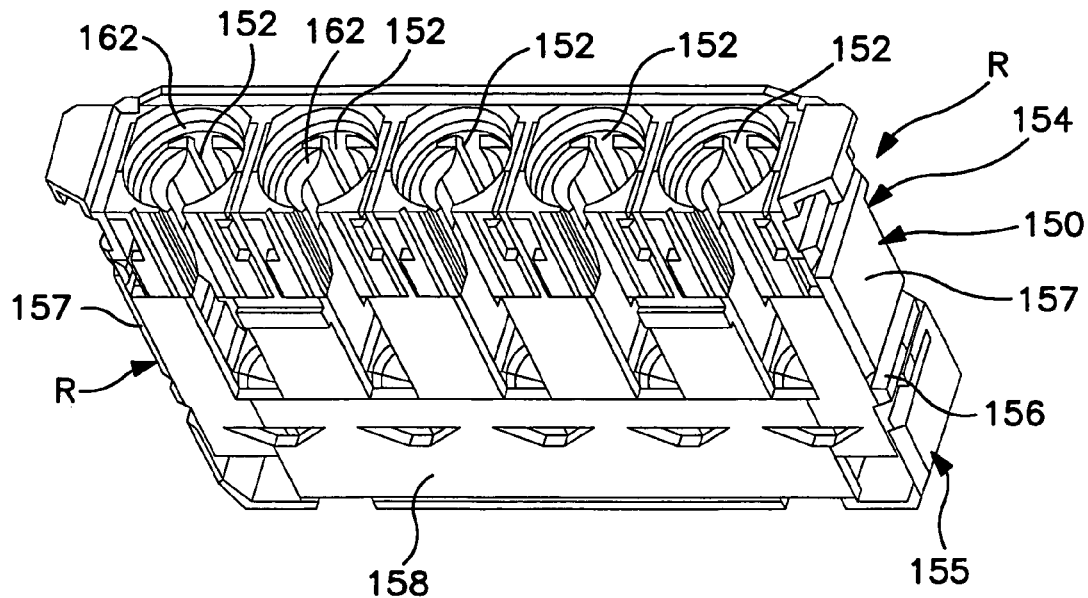
FIGS. 11A and 11B are top-front side and bottom-rear side perspective views, respectively, of a preferred specimen-container rack adapted for use with the magnetic specimen-transport system of the invention.
Figure 11B:
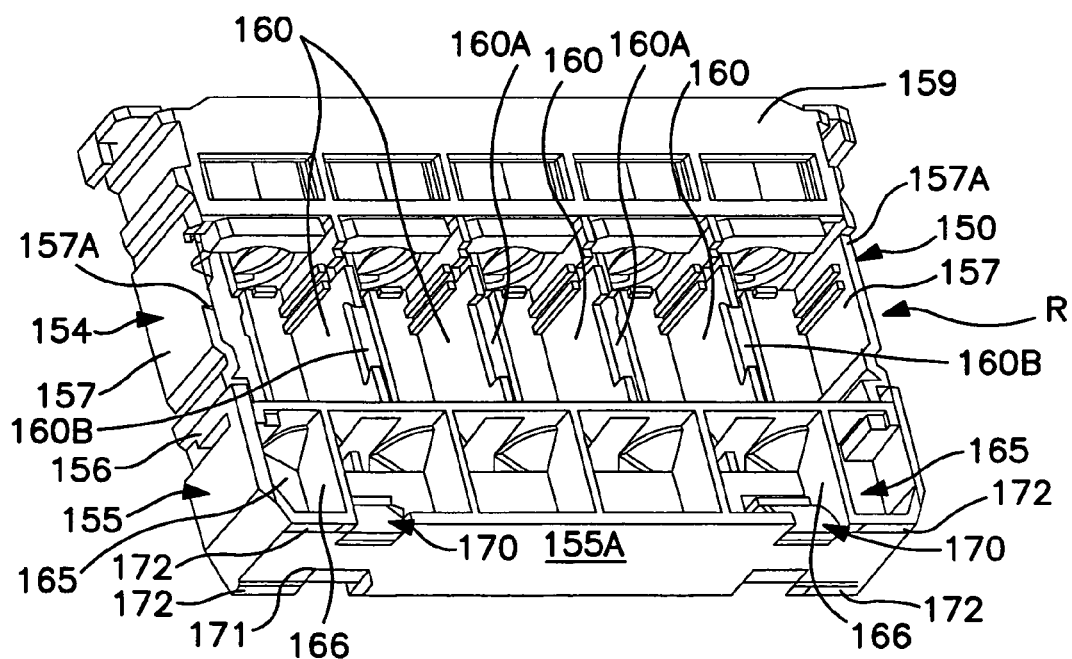

In the embodiment shown, housing 150 is made of plastic and comprises two interlocking sections, an upper section 154 that defines the container compartments 152, and a base section 155 that provides support for the specimen containers received by the rack, and further serves to house the above-noted magnetically-attractive members 170. The two sections are snapped together and held in place by a pair of flexible arms 156 provided at opposite ends of the base section. In FIGS. 11A and 11B, the upper section of the rack is shown as comprising a pair of parallel end walls 157 disposed at opposite ends of a forward wall 158 and a rear wall 159. A plurality of equally-spaced transverse walls 160 extend between the front and rear walls. The transverse walls operate to separate each the container compartments 152. At the top of each compartment, a container-centering assembly 162 is provided. The latter serves to releasably engage and to center specimen containers of different diameters within the compartments, whereby the central longitudinal axes of the received containers are equally spaced and arranged in parallel in a common plane. Thus, when such a specimen-container rack is registered in its specimen-aspiration position within a specimen-transport module, the aspiration probe assembly can repeatedly and reliably access the center of each of the specimen containers by moving sideways (along the X coordinate) in a vertical plane. Details of the centering assemblies 162 are described in the commonly assigned U.S. Pat. No. 5,687,849, incorporated herein by reference. The engaging force between the container-centering assembly and the container is sufficient to prevent the container from rotating or moving axially during the specimen-mixing operation when the containers are repeatedly inverted.

As shown in FIG. 11B, the rear, vertical edge of walls 157 and 160 are provided with structure that accommodates a horizontally-extending tongue member 47A that protrudes from the mounting plate 47 of the mixing device 46. Such structure takes the form of series of spaced notches 157A, 160A and 160B. Whereas notches 157A and 160A are rectangular in shape and provide clearance for the tongue member 47A, notches 160B have a trapezoidal shape that is adapted to engagingly receive the opposing edges of the tongue member 47A (which has a trapezoidal transverse cross-section), as the rack is caused to slide horizontally along the surface of mixing plate 47 by the magnetic transport system described above. Preferably, the trapezoidal notches are formed in the edges of walls 160 that separate the first and second compartments 152, and the forth and fifth compartments 152. The dimensions of the rectangular notches 157A and 160A are such as to enable the tongue member 47A to slide unimpededly along wall 47 to engage the notches 160B. Upon completing engagement between the two notches 160B and tongue 47A, the specimen-container rack is in a position to be inverted by the mixing device 46, causing the contained specimens in the rack to be mixed, and to have the aspiration probe assembly PA of an associated clinical instrument access any one of the specimen containers supported by the rack.

Figure 12:
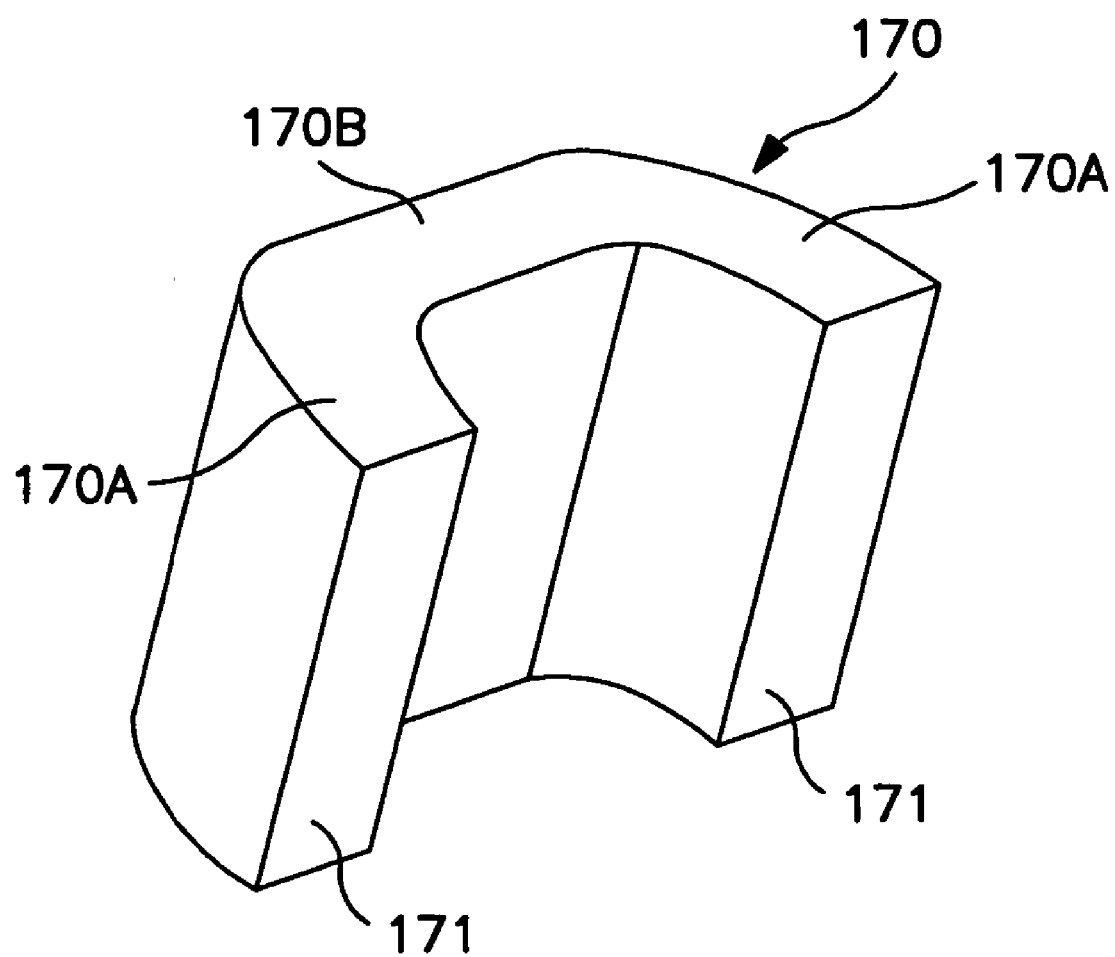
FIG. 12 is a perspective illustration of a magnetically-attractive member that is adapted to be mounted within the bottom portion of the rack shown in FIGS. 11A and 11B.

In order to render the rack susceptible to being advanced on surface S by the underlying magnetic transport mechanism described above, the base section 155 of rack housing 150 is structured to receive and support a pair of U-shaped, magnetically-attractive members 170 (best shown in FIG. 12). Preferably, each member 170 comprises a ferromagnetic material, most preferably magnetically-attractive stainless steel 440C. Each member 170 comprises a pair of spaced leg portions 170A that are connected together at one end by a bridge portion 170B. Members 170 are supported in the rack's base portion so that the distal ends 171 of their respective leg portions 170A extend downwardly, toward the bottom surface 155A of the rack. As shown in FIG. 11B, the bottom surface of the rack defines four rectangular pads 172 which protrude downwardly, by about 0.5 mm., at the four corners of the rack. These pads provide the only physical contact between the rack and the transport surface S. Preferably, the distal ends 171 of members 170 terminate about 0.5 mm. short of, the plane of the pads 172. The spacing between the distal ends 171 corresponds to the spacing between the pole tips of the permanent magnets 88 and 90 carried by the magnetic truck 86. Preferably, this spacing is about 9.5 mm. Thus, when a specimen-container rack is resting on its pads 172 atop surface S with the distal ends of members 170 being juxtaposed to the pole tips of magnets 88 and 90, a magnetic circuit will be completed, with the flux emanating from one magnetic pole tip passing through member 170 and entering the opposite pole tip. The strength of the magnetic pole pieces is selected to provide a sufficient magnetic coupling between the rack and the drive mechanism to impart motion to the rack as the magnetic drive moves below surface S. The provision of opposing U-shape structures, one for the permanent magnets 96 and 98 and the other for the magnetically-attractive members 170, gives rise to a magnetic coupling that strongly resists lateral decoupling forces while being relatively compliant to vertical decoupling forces.

In use, the X/Y magnetic transport system of the invention operates under the control of the system controller to initially position the magnetic truck beneath the first rack in the input queue 41, i.e., the rack positioned adjacent the guide member G1 shown in FIG. 4. In doing so, it should be noted that the mechanism used to forwardly advance racks within the input queue can only forwardly advance a single rack to a position in which it would be the third rack back from the guide plate G1. Thus, to assure that the magnetic transport mechanism operates to magnetically capture a rack in the input buffer when only one or two racks are in the input queue, the magnetic transport mechanism will "enter" the input buffer, from below plate P, of course, at a location underlying the third rack from the front. Upon entering the input buffer as noted, the magnetic drive mechanism will magnetically engage the rack in the third rack back position. If the rack engaged is the only rack in the queue, the transport mechanism will advance it into the registration position adjacent guide member G1 by moving in the Y-direction. Thereafter, the transport mechanism will move the rack edgewise along transport path D as described above. If two racks are in the input queue, the transport mechanism will magnetically capture the second rack back in the queue, which will be located in the third rack back position, and it will advance both racks forward, pushing the first rack ahead of the second until the first rack contacts guide member G1, at which point the racks will be prevented from moving further forward. However, the transport mechanism will continue moving forward in the Y-direction, thereby decoupling the transport magnets from their previous interaction with the second rack, and coupling these magnets with the magnetically-attractive members of the first rack. As will be appreciated, in the event that there are three or more magnets in the input queue, the same process will be repeated, in which case the transport magnets are coupled and de-coupled twice before they finally couple with the first rack in the queue. Once magnetically coupled to the first rack in the input queue, the magnet transport mechanism remains couple to the rack until the rack has reached its next destination.

From the foregoing, it will be appreciated that a new and advantageous magnetic transport system has been devised for advancing magnetically attractable specimen-container racks along mutually perpendicular paths relative to a clinical instrument. While the invention has been disclosed with reference to a particularly preferred embodiment, it will be appreciated that changes can be made to the disclosed embodiment without departing from the spirit of the invention, and resort should be had to the appended claims in determining the scope of the invention.

What is claimed is:

1. A magnetic transport system for transporting racks of specimen-containers atop a featureless rack-supporting surface of a non-magnetic support plate, each of said specimen-container racks having a bottom surface configured to be supported by said rack-supporting surface, and having a plurality of magnetically-attractive members that are spacedly arranged in close proximity to said bottom surface, said magnetic transport system comprising:

a first bi-directional linear drive mechanism constructed to selectively move a truck in opposite directions along a first linear path closely spaced from a bottom side of said non-magnetic support plate, said truck comprising a movably-mounted plate that supports a plurality of spaced magnetic field-producing devices, each of said devices comprising a U-shaped permanent magnet having opposing poles extending in the same direction and being effective to produce a magnetic field atop said non-magnetic support plate when said truck is moving along said first linear path, said magnetic fleid being sufficiently strong to magnetically engage said magnetically-attractive members of a specimen-container rack positioned on said rack-supporting surface of the non-magnetic support plate and cause such specimen-container rack to move along said rack-supporting surface of the non-magnetic support plate as the truck is moved along said first linear path by said first bi-directional linear drive mechanism, said magnetic field producing devices being arranged on the truck in a pattern consistent with the arrangement of the magnetically attractive members of the specimen-container rack so that each of the respective magnetic fields produced by said magnetic field-producing devices interacts with a magnetically-attractive member of said rack.

2. The magnetic transport system of claim 1 further comprising a second independent bi-directional linear drive mechanism, said second linear drive mechanism supporting said first bi-directional linear drive mechanism for selective movement in opposite directions along a second linear path that is generally perpendicular to said first linear path and being operable to selectively advance said first linear drive mechanism along said second linear path, said magnetic field-producing devices being effective to produce a magnetic field atop said non-magnetic support plate that is sufficiently strong to magnetically engage said magnetically-attractive members of a specimen-container rack positioned on said support surface of the non-magnetic support plate and to cause the specimen-container rack to move atop said featureless support surface in mutually perpendicular directions as said truck is moved along said first linear path by the first bi-directional linear drive mechanism, and as said first bi-directional drive mechanism is moved along said second linear path by said second bi-directional linear drive mechanism.

3. The magnetic transport system of claim 2 wherein each of said plurality of spaced magnetic field-producing devices supported by said truck plate comprises a U-shaped permanent magnet having opposing poles extending in the same direction.

4. The magnetic transport system of claim 3 wherein each of said plurality of magnetically-attractive members of said specimen container racks comprises a U-shaped ferromagnetic member having a pair of spaced legs that are arranged to magnetically interact with the opposing poles of said U-shaped permanent magnets supported by said truck plate.

5. The magnetic transport system of claim 4 wherein each of said U-shaped ferromagnetic members comprises magnetically-attractive stainless steel.

6. The magnetic transport system of claim 2 wherein each of said plurality of spaced magnetic field-producing devices supported by said truck plate comprises a U-shaped assembly comprising a pair of spaced, parallel bar magnets, each having opposing magnetic poles, and an interconnecting flux bridge that connects opposing magnetic poles of said bar magnets.

7. The magnetic transport system of claim 6 wherein each of said bar magnets comprises a neodymium-doped iron, and said flux bridge comprises an iron bar.

8. The magnetic transport system of claim 1 wherein each of said plurality of spaced magnetic field-producing devices supported by said truck plate comprises a U-shaped assembly comprising a pair of spaced, parallel bar magnets, each having opposing magnetic poles, and an interconnecting flux bridge that connects opposing magnetic poles of said bar magnets.

9. The magnetic transport system of claim 8 wherein each of said bar magnets comprises a neodymium-doped iron, and said flux bridge comprises an iron bar.

10. The magnetic transport system of claim 1 wherein each of said plurality of magnetically-attractive members of said specimen container racks comprises a U-shaped ferromagnetic member having a pair of spaced legs that are arranged to magnetically interact with the opposing poles of said U-shaped permanent magnets supported by said truck plate.

11. The magnetic transport system of claim 10 wherein each of said U-shaped ferromagnetic members comprises magnetically-attractive stainless steel.

12. The magnetic transport system of claim 10 wherein one of said plurality of magnetically-attractive members is positioned at each of the opposing ends of said specimen container racks.

13. The magnetic transport system of claim 1 wherein one of said plurality of magnetically-attractive members is positioned at each of the opposing ends of said specimen container racks.

14. A magnetic transport system for transporting racks of specimen-containers atop a featureless rack-supporting surface of a non-magnetic support plate, each of said specimen-container racks having a bottom surface configured to be supported by said rack-supporting surface, and having a plurality of magnetically-attractive members that are spacedly arranged in close proximity to said bottom surface, said magnetic transport system comprising:

(a) a first bi-directional linear drive mechanism constructed to selectively move a truck in opposite directions along a first linear path closely spaced from a bottom side of said non-magnetic support plate, said truck comprising a movably-mounted plate that supports a plurality of spaced magnetic field-producing devices, each of said devices being effective to produce a magnetic field atop said non-magnetic support plate when said truck is moving along said first linear path, said magnetic field being sufficiently strong to magnetically engage said magnetically-attractive members of a specimen-container rack positioned on said rack-supporting surface of the non-magnetic support plate and cause such specimen-container rack to move along said rack-supporting surface of the non-magnetic support plate as the truck is moved along said first linear path by said first bi-directional linear drive mechanism, said magnetic field producing devices being arranged on the truck in a pattern consistent with the arrangement of the magnetically attractive members of the specimen-container rack so that each of the respective magnetic fields produced by said magnetic field-producing devices interacts with a magnetically-attractive member of said rack; and (b) a second bi-directional linear drive mechanism, said second linear drive mechanism being independent from said first bi-directional linear drive mechanism and serving to support said first bi-directional linear drive mechanism for selective movement in opposite directions along a second linear path that is generally perpendicular to said first linear path, said second bi-directional linear drive mechanism being operable to selectively advance said first linear drive mechanism along said second linear path, said magnetic field-producing devices being effective to produce a magnetic field atop said non-magnetic support plate that is sufficiently strong to magnetically engage said magnetically-attractive members of a specimen-container rack positioned on said support surface of the non-magnetic support plate and to cause the specimen-container rack to move atop said featureless support surface in mutually perpendicular directions as said truck is moved along said first linear path by the first bi-directional linear drive mechanism, and as said first bi-directional drive mechanism is moved along said second linear path by said second bi-directional linear drive mechanism.

* * * * *